United States Patent [19]

Barrows

[11] 4,071,891
[45] Jan. 31, 1978

[54] ELECTRONIC CALCULATOR - REGISTER FOR HEMATOLOGY DIFFERENTIALS

[76] Inventor: George H. Barrows, 1279 Bassett, Louisville, Ky. 40204

[21] Appl. No.: 682,149

[22] Filed: Apr. 30, 1976

[51] Int. Cl.² .................. G06F 15/42; G01N 33/16
[52] U.S. Cl. ...................... 364/416; 128/2 G; 235/92 PC; 356/39; 364/555; 364/715
[58] Field of Search .......... 235/152, 156, 92 PC, 235/151.35; 356/39, 40; 128/2 R, 2 G

[56] References Cited

U.S. PATENT DOCUMENTS

| | | | |
|---|---|---|---|
| 3,315,229 | 4/1967 | Smithline | 235/92 PC |
| 3,740,143 | 6/1973 | Groner et al. | 356/39 |
| 3,760,171 | 9/1973 | Wang et al. | 235/156 |
| 3,813,533 | 5/1974 | Cone et al. | 235/156 |
| 3,892,958 | 7/1975 | Tung | 235/156 |
| 3,907,437 | 9/1975 | Hirschfeld | 356/39 X |
| 3,916,205 | 10/1975 | Kleinerman | 356/39 X |
| 3,919,530 | 11/1975 | Cheng | 128/2G X |
| 3,922,532 | 11/1975 | Kitchener et al. | 235/92 PC X |
| 3,924,111 | 12/1975 | Farris | 235/156 |
| 3,939,334 | 2/1976 | Roth et al. | 235/156 |
| 3,946,218 | 3/1976 | Rode et al. | 235/156 |

*Primary Examiner*—Jerry Smith

[57] ABSTRACT

An electronic tabulator for computing and displaying running totals of six different cells as well as a running total of the combined cell count. Means are also provided for dividing the individual cell count by the total cell count to express the individual cell counts as a percentage of the total. In a preferred embodiment, a keyboard provides data entry to seven commercially available calculator chips which compute the running totals and individual percentages as well as provide an output to individual LED displays.

8 Claims, 8 Drawing Figures

ELECTRONIC CALCULATOR - REGISTER FOR HEMATOLOGY DIFFERENTIALS

BACKGROUND OF THE INVENTION

The present invention relates to an electronic instrument for counting and totalizing a plurality of different types of blood cells or other biological cells and expressing the individual cell counts as a percentage of the total count.

Differential cell counts are an important aspect of testing in medical and other biological laboratories. A white blood cell differential is one of the most commonly performed counts. Other differential counts include maturation index in PAP smears, leukocyte alkaline phophatase, and barr body counts.

The apparatus currently employed by laboratories for computing hematological differantials and other cell counts are mechanical counters or electrically operated mechanical step counters. These range from very simple counters which are capable of providing running totals of two types of cells to counters which are capable of totalizing nine different types of cells as well as a total of all cells counted. In order to express the individual cell counts as percentages of the total, which is the most commonly used method for rendering a meaningful expression of the cell counts, is to terminate the count when the total of all cells counted reaches 100. At this point, the individual percentages are equal to the total count expressed for each of the cell types. A problem which often arises, however, is that the technician may not stop when the total count reaches 100 thereby necessitating manual computation to determine the percentage value for each type of cell. This is a time consuming operation and often causes technical errors. This may result in an erroneous cell differential leading to an incorrect diagnosis on the part of the physician utilizing the laboratory data.

A further disadvantage to the necessity for terminating the count at 100 cells or ten factor multiples thereof is that it may be desirable for all the cells on a certain slide to be counted. In this case, it is imperative that the percentage calculation be made.

The mechanical counters are cumbersome to operate and may fail to register an intended entry. Additionally, many of the mechanical counters do not provide means for deleting an erroneously entered count. Many counters have no means for preventing the simultaneous entry of two individual counts leading to another source of inaccurate entries.

By necessity, the prior art counters employ intricate mechanical components and are therefore costly to manufacture and require a certain amount of maintenance to enable them to operate smoothly and accurately. Mechanical components also impose certain size and weight contraints on the apparatus as well as power requirements where the mechanical registers are actuated by electromechanical devices.

It is therefore, an object of the present invention to provide an electronic calculator-register which is capable of providing running totals of individual cell counts as well as a total cell count and means for calculating the percentage of the individual counts to the whole at any time during the count.

It is also an object of the present invention to provide a calculator-register for cell differentials wherein the running totals and the individual cell percentages are conveniently displayed.

It is a further object of the present invention to provide a calculator-register for cell differentials which is of solid state construction employing a minimum of mechanical elements thereby resulting in a unit which is small in size and highly responsive and reliable in its operation.

A further object of the present invention is to provide an electronic calculator-register capable of rapidly and accurately providing individual cell percentages by means of simple keyboard entries regardless of the total cell count.

Another object of the present invention is to provide an electronic calculator-register for cell differentials wherein double count entries are prevented.

Yet another object of the present invention is to provide an electronic calculator-register for cell differentials which permits easy deletion of incorrectly entered counts.

A still further object of the present invention is to provide an electronic caculator-register for cell differentials including audible means for signaling the technician when a single cell count has been entered and for providing a different audible signal when 100 counts have been entered.

Yet another object of the present invention is to provide an electronic calculator-register for cell differentials which can be economically mass manufactured at a low unit cost.

These and other object of the present invention will be apparent from the detailed description together with the appropriate drawings.

SUMMARY OF THE INVENTION

An electronic calculator-register for hematology differentials comprising manually operable data entry means having a first plurality of manually actuated input elements, each input element having means for entering data signifying a single event when actuated; the data entry means having a second plurality of manually actuated input elements for entering numerical data and instructional commands; computation means having a plurality of channels operatively connected to the data entry means for storing the data entered therein and performing mathematical computations on the entered data in response to instructional commands; the computation means including channel register means associated with each of the channels and operatively connected to the first plurality of input elements for computing and storing individual running totals of the number of events entered by each of the input elements and a total register means for computing and storing a collective running total of the number of events entered by the first input elements collectively; the computation further including means for storing numerical representing the collective running total entered therein by the second plurality of input elements and performing a mathematical operation involving the entered numerical data and the individual running totals to convert each individual total to a number equal to the decimal fraction of the particular individual total to the collective total; and display means for concurrently displaying the individual and collective totals before the mathematical operation and for concurrently displaying the decimal fractions after the mathematical operation.

DETAILED DESCRIPTION

In basic terms, the calculator-register of the present invention comprises a single keyboard which has a plurality of outputs to seven separate channels through a switching and pulse generating network which permits separate running totals to be stored and displayed by six of the channels and a running total of the combined count stored in the seventh channel. In the calculate mode, each of the totals stored in the individual channels are divided by the combined total count to display the individual count as a percentage of the total.

Figure 1:
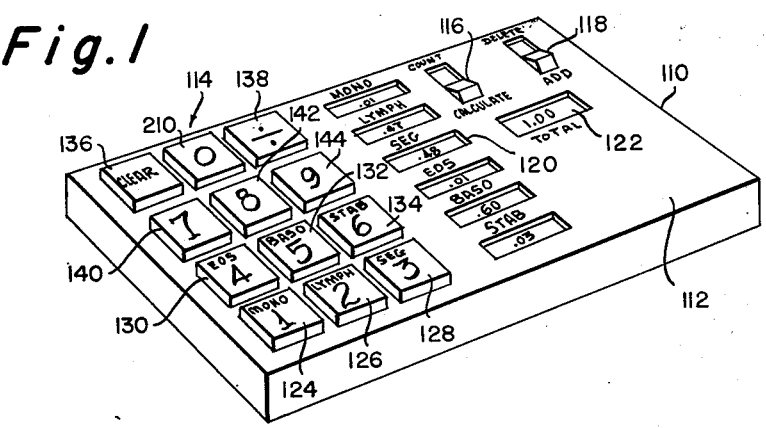
FIG. 1 is a pictorial perspective view of the calculator-register of the present invention illustrating the keyboard and displays.

With reference to FIG. 1, the calculator-register is illustrated and comprises a case 110 having a face plate 112 on which are mounted a plurality of manually operable keys comprising keyboard 114 for the entry of data, and mode switches 116 and 118, the latter serving to switch the device between the Count and Calculate modes and Delete and Add modes, respectively. Also present on the face plate 112 are six windows 120 which permit viewing of LED readouts which display the data presently stored in each of the channels. Another window 122 permits viewing of the LED readouts associated with the total cell count channel.

The case 110 and face plate 112 may be made of plastic or various metals or other forms of structural materials. Switches 116 and 118 are preferably slide switches and the keys of keyboard 114 are of the standard spring loaded single pole type employed in hand-held calculators which close switches when depressed. Keys 124, 126, 128, 132 and 134 carry the decimal numbers 1 through 6 and are also provided with indicia representing the particular type of cell being entered. For example, key 124 is depressed to enter a single count for monocytes, key 126 for lymphocytes, key 128 for neutrophils, key 130 for eosinophils, key 132 for basophils and key 134 for stabs. Windows 120 have appropriate indicia associated with them corresponding to the indicia keys 124-134. If desired the indicia on keys 124-134 could be varied depending on the particular count being performed. Key 136 is a clear function and key 138 the division function entry switch. Due to the fact that solid state circuitry is employed, the tabulator may be relatively small in size so that it is highly portable and capable of hand-held operation.

Figure 2:
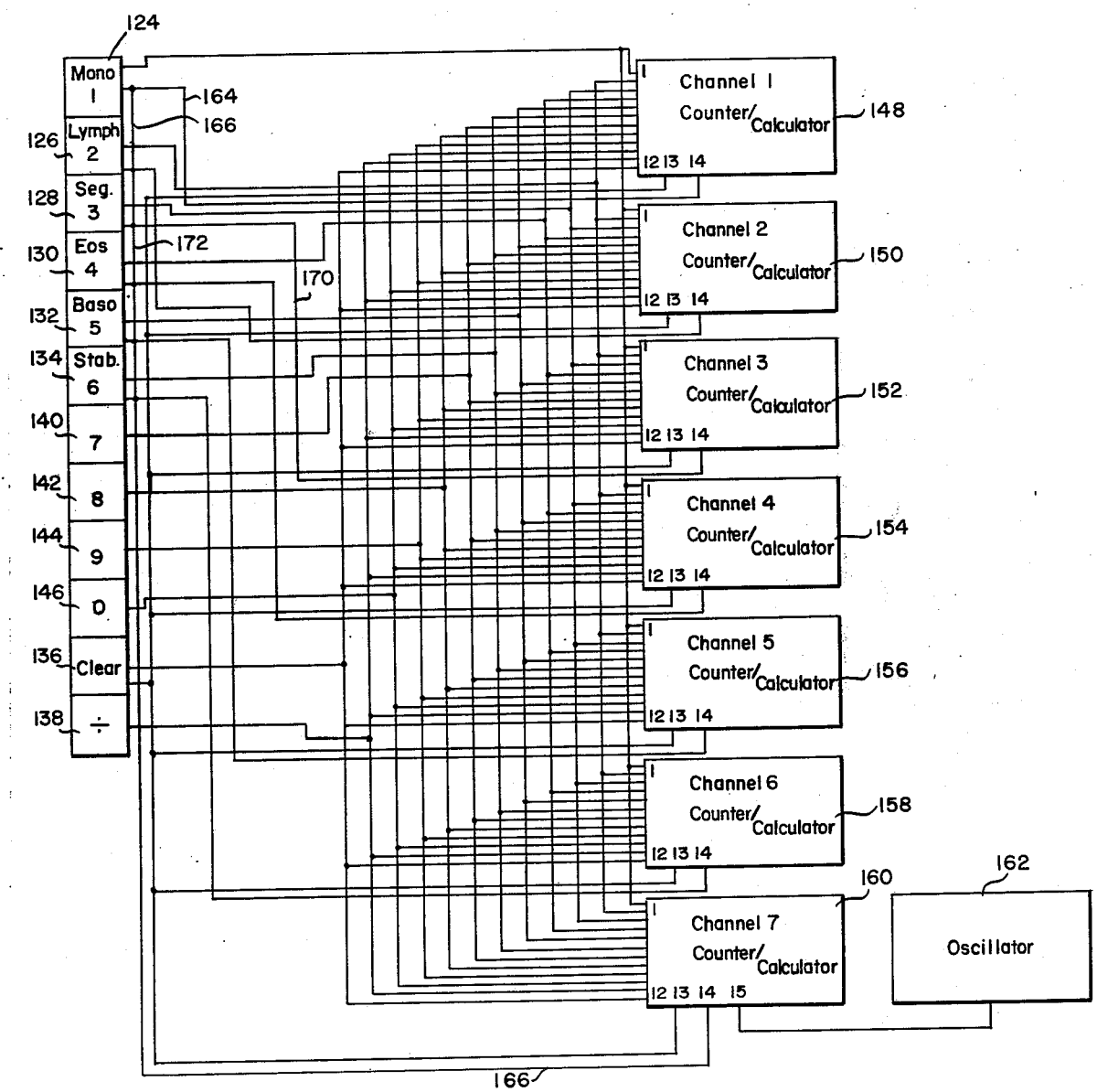
FIG. 2 is a simplified block diagram of the invention showing the general relationship between the keyboard and the counter/calculator chips.

In FIG. 2, the relationship between the keyboard entries and the individual counter/calculators is illustrated. This is a greatly simplified diagram and merely represents the various flow paths of data entered by the keys.

Corresponding to FIG. 1, keys 124-134 carry indicia identifying the particular cells being counted as well as decimal intergers 1 through 6. Keys 140, 142, 144 and 146 are identified with the decimal intergers 7, 8, 9 and 0, respectively and keys 136 and 138 the clear function and division function, respectively. Associated with keys 124-138 are a plurality of counter/calculators 148, 150, 152, 154, 156, 158 and 160 wherein counter/calculators 148-158 comprise channels 1 through 6 and counter/calculator 160 constitutes channel 7, which is the total cell count channel. An oscillator 162 is associated with the total counter/calculator 160 to provide an audible signal whenever an entry is made therein.

Keys 124-134 are dual function in nature and activate different circuits depending on whether the device in the Count or Calculate mode as controlled by the position of slide switch 116. In the count mode, the depression of keys 124 enters an integer 1 in counter 148 through path 164 and in counter 160 through path 166. Subsequent depression of keys 124 will enter a second integer 1 in counters 148 and 160 and add this integer to the sum previously stored therein. In a similar fashion, depression of keys 128 will enter an integer 1 in counter 152 through path 170 and will enter an integer 1 in counter 160 through path 172 and 166. The remainder of keys 124-134 are associated with counter/calculators 148-160 in the same manner and cause an integer 1 to be added to the sum presently stored in its respective counter as well as adding an integer 1 to the collective sum stored in counter 160. Each time that an integer 1 is entered into counter 160, oscillator 162 will emit an audible signal to notify the technician that the entry has been made. In the Count mode, keys 140, 142, 144, 146 and 138 are not operable. Depression of key 136 when the device is in the Count mode causes the totals stored in each of the counter/calculators 148-160 to be cleared.

When switch 116 is moved to the Calculate position, all the switches 124-146 are rendered operable to enter numerical data into all of the counter/calculators 148-160 simultaneously. In the Calculate mode, depression of switch 124 will enter an integer 1 in all of the counter/calculators; actuation of key 128 will enter an integer 3 in all of the counter/calculators; actuation of key 142 will enter an integer 8 in all of the counter/calculators. If keys 126, 132 and 134, for example, are actuated in sequence, the number 256 will be entered in all of the counter/calculators 148-160. Following the entry of any numerical data, the actuation of divide-by key 138 followed by the entry of another number and then the reactuation of key 138 will cause the first entered number to be divided by the second number. In the Calculate mode, the actuation of key 136 at any time will cause the divisor to be cleared.

Figure 3A:
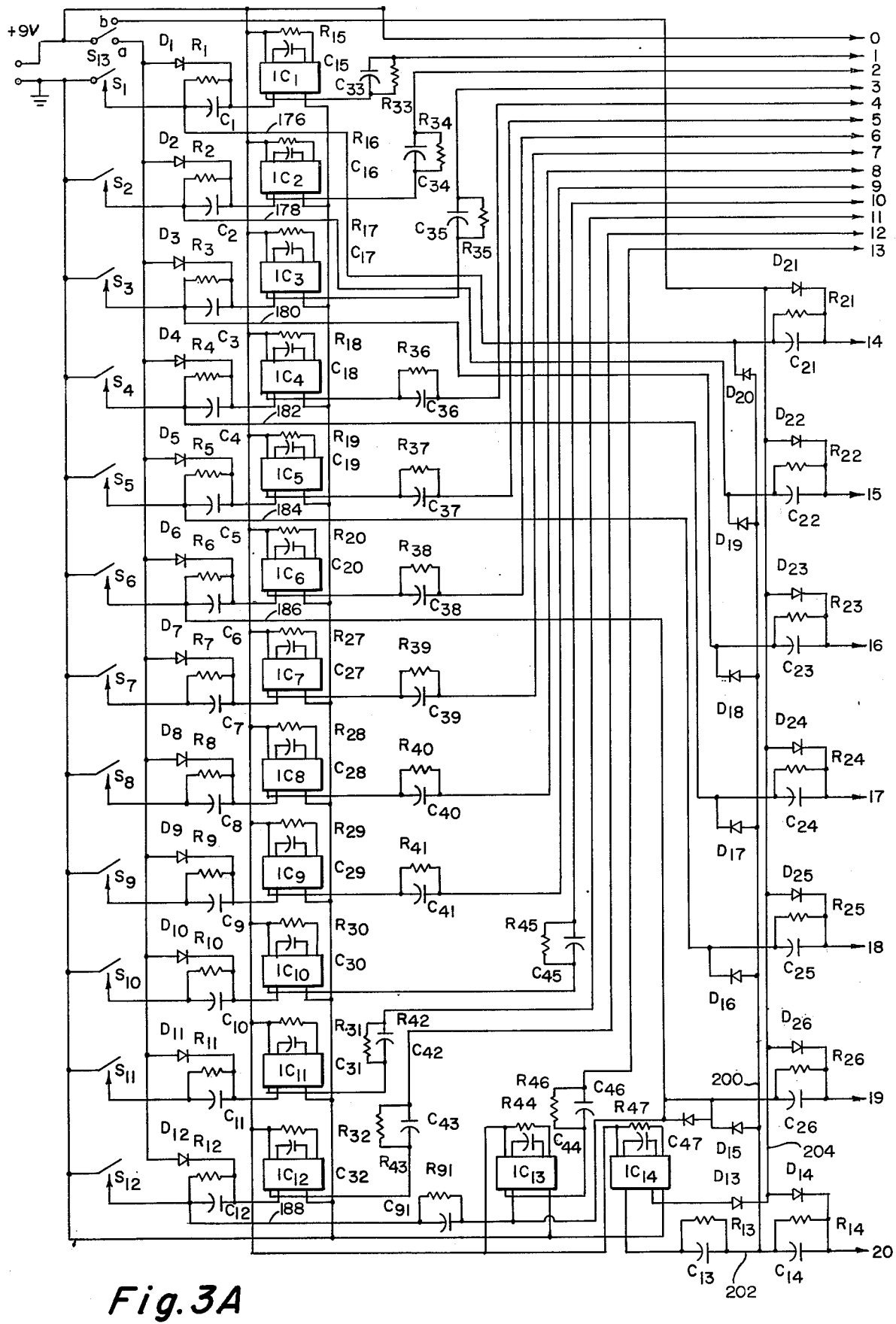
FIGS. 3A-3C are a composite electrical diagram of the present invention showing the keyboard switching and intermediate switching and pulsing circuitry in detail.
Figure 3B:
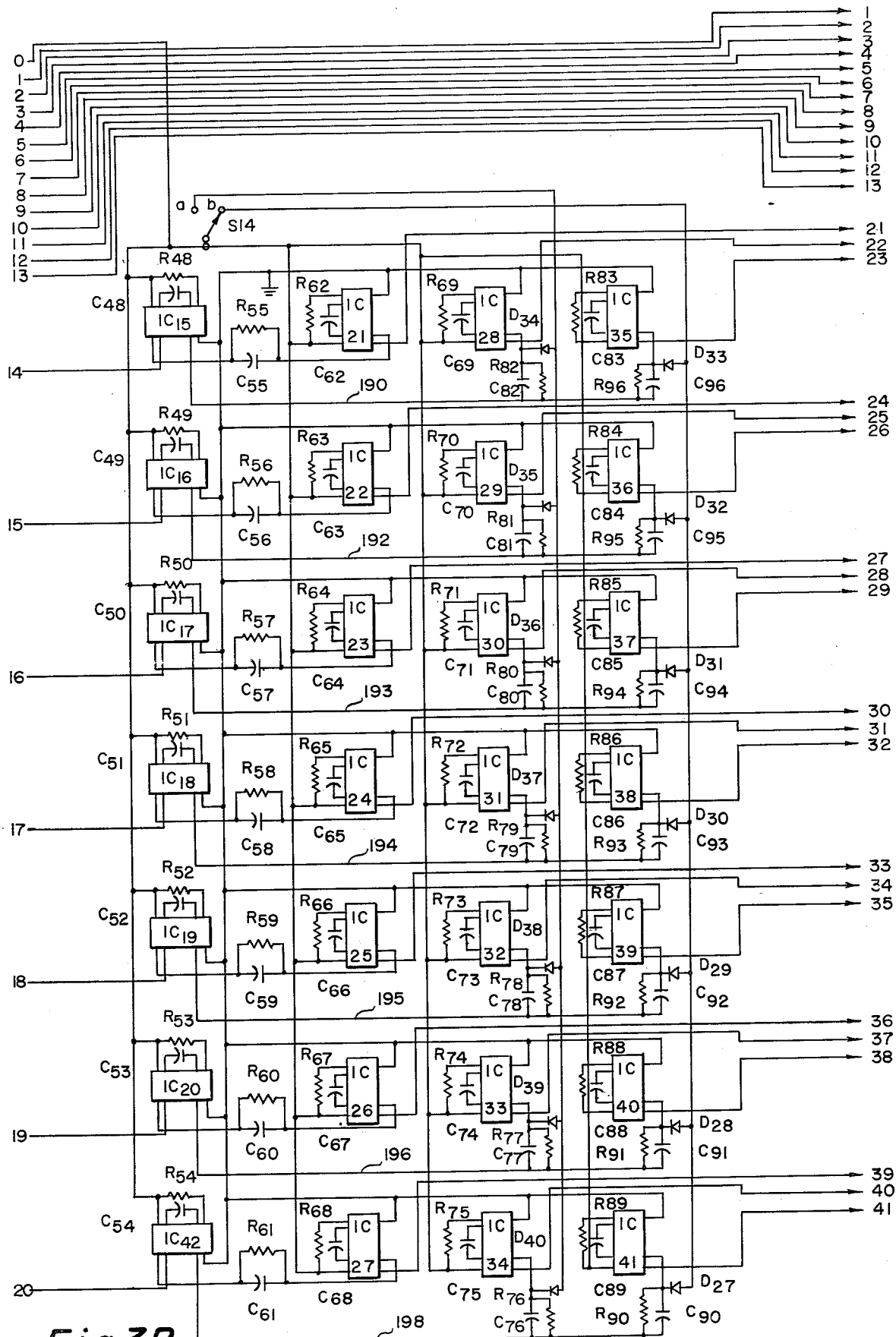
Figure 3C:
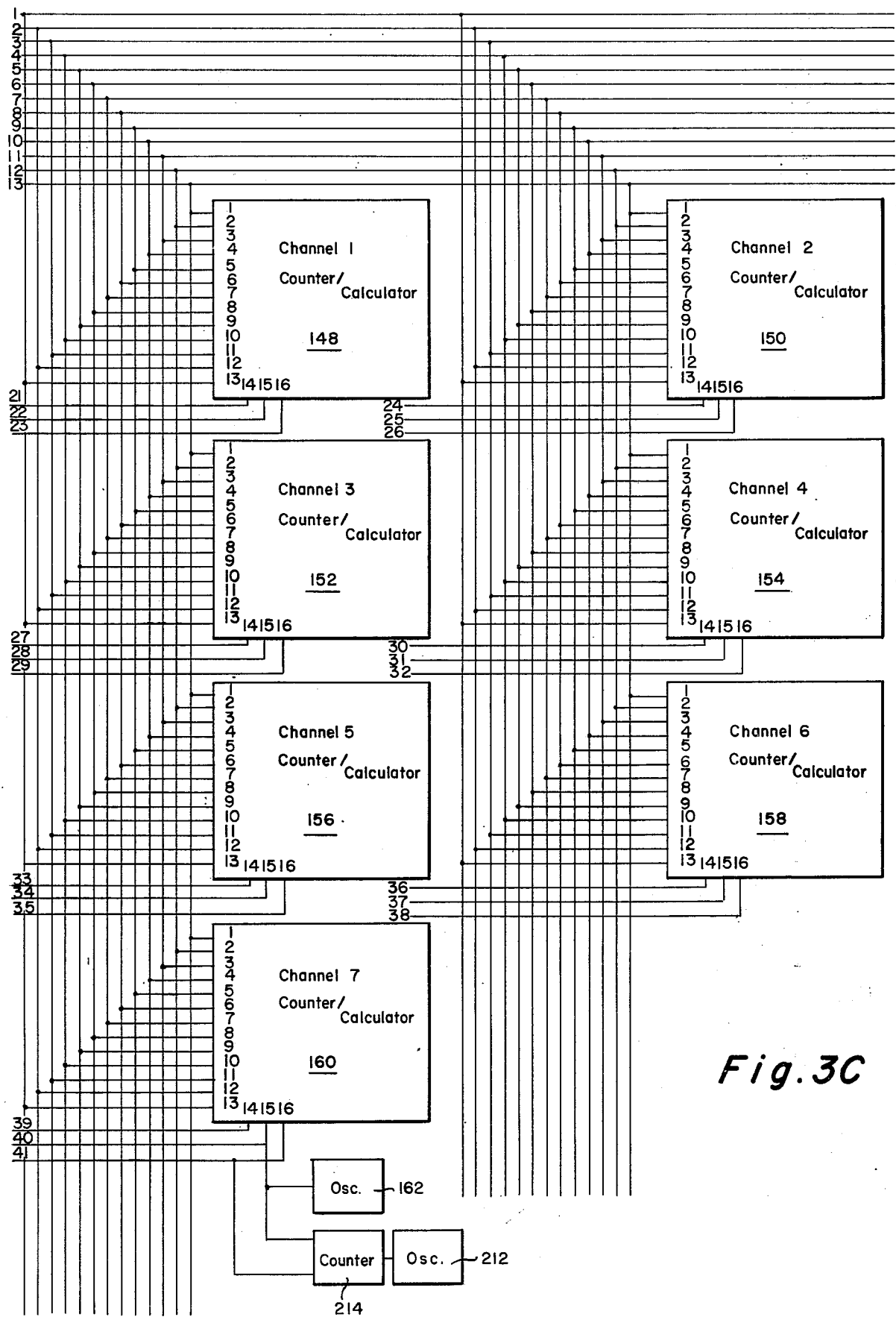

Briefly, the apparatus operates as follows. Switch 116 is moved to the Count position and switch 118 to the Add position. As the technician observes the blood sample under the microscope, he depresses one of switches 124-134 each time that particular cell is observed thereby entering an integer 1 into the counter/calculator 148-158 associated with the particular cell and an integer 1 into counter/calculator 160 which stores a count of the total number of cells observed. Should an incorrect entry be made, switch 118 may be moved to the Delete position and the particular key 124–134 with which the incorrect entry was made is actuated so that an integer 1 is deleted from its respective counter/calculator as well as from the total counter/calculator 160. When a total of 300 cells, for example, have been observed, switch 116 is moved to the Calculate position and the total number (in this case 300) observed through display window 122 is intered into all of the channels by depressing key 138 once, key 128 once and key 146 twice. At this point, the number 300 will appear in windows 120 and 122. Key 138 is then depressed a second time causing the individual and the total counts to be divided by the number 300 and the quotient to appear in windows 120 and 122. The numbers so appearing represent the percentage of each of the individual cells in relation to the total number of cells counted. FIGS. 3A, 3B and 3C constitute a detailed composite circuit diagram of the present invention of which FIG. 2 is a general representation. The right portion of FIG. 3A joins with the left portion of FIG. 3B at points 0–20 and the right portion of FIG. 3B joins with FIG. 3C at points 0 through 13 and 21 through 41.

Switch $S_{13}$ corresponds to slide switch 116 and is operative to switch the device between the Count and Calculate mode by placing a 9 volt inhibit voltage on monostable multivibrators $IC_1$–$IC_{12}$ through diodes $D_1$–$D_{12}$ in the Count mode. Multivibrators $IC_1$–$IC_{12}$, which are SN 74121 multivibrators, receive this 9 volt inhibit voltage at pins 3. In the Calculate mode, switch $S_{13}$ is moved to the "$b$" position thereby placing a 9 volt inhibit on multivibrators $IC_{13}$, $IC_{15}$–$IC_{20}$ and $IC_{42}$ through diodes $D_{15}$, $D_{21}$–$D_{26}$ and $D_{14}$.

Switches $S_1$–$S_{10}$ correspond to keys 124–146, switch $S_{11}$ corresponds to divide-by key 138 and switch $S_{12}$ to key 136 so that when the respective key is depressed by the technician, its corresponding switch $S_1$–$S_{12}$ is closed. In the Calculate mode, the closing of any of switches $S_1$–$S_{12}$ causes a negative impulse to trigger its respective monostable multivibrator $IC_1$–$IC_{12}$ through resistor-capacitor circuits $R_1C_1$–$R_{12}$-$C_{12}$. When these monostable multivibrators are triggered, a 20 millisecond negative impulse is generated and fed into counter/calculators 148–160 through the appropriate line 1 through 12. The 20 millisecond impulse is taken from multivibrators $IC_1$–$IC_{12}$ off pin 1 and passes through blocking circuit $R_{33}C_{33}$––$R_{41}C_{41}$ for multivibrators $IC_1$–$IC_9$, respectively, through $R_{45}C_{44}$ for $IC_{10}$, through $R_{42}C_{42}$ for $IC_{11}$ and through $R_{43}C_{43}$ for $IC_{12}$. By adjusting the value of the resistor-capacitor circuit for multivibrators $IC_1$–$IC_{12}$, such as $R_{15}$ and $C_{15}$ for $IC_1$ and $R_{18}C_{18}$ for $IC_{4A}$, the duration of the output pulse can be adjusted. By virtue of the connection scheme illustrated in FIG. 3C, the output pulse from any one of multivibrators $IC_1$–$IC_{12}$ will be entered in each of counter/calculators 148–160. As mentioned previously, in the Calculate mode each of the switches $S_1$–$S_{10}$ causes the entry of integers 1 through 0, respectively. Similarly, the closing of switch $S_{11}$ enters an instructional command for the division function and the closing of switch $S_{12}$ causes the divisor to be cleared. The details of this will be described at a later point.

In the Count mode, switch $S_{13}$ is in position $a$ thereby placing a 9 volt inhibit voltage on monostable multivibrators $IC_1$–$IC_{12}$ and multivibrators $IC_{13}$–$IC_{20}$ and $IC_{42}$ are released. Upon the closing of one of switches $S_1$ through $S_6$ and switch $S_{12}$, a negative going impulse travels through line 176–188, respectively, to pin 3 of the respective multivibrators $IC_{13}$, $IC_{15}$–$IC_{20}$ and $IC_{42}$.

For example, the closing of switch $S_2$ causes the negative going impulse to trigger $IC_{16}$ through line 176, closing of switch $S_5$ triggers $IC_{19}$ through line 184 ad the closing of switch $S_{12}$ triggers $IC_{13}$ through line 188.

When multivibrators $IC_{15}$, $IC_{16}$, $IC_{17}$, $IC_{18}$, $IC_{19}$, $IC_{20}$ or $IC_{42}$ are triggered, they produce a negative going pulse of 25 milliseconds duration at pin 1 which triggers its adjacent multivibrator $IC_{21}$, $IC_{22}$, $IC_{23}$, $IC_{24}$, $IC_{25}$, $IC_{26}$, $IC_{27}$, respectively, through the intermediate resistor-capacitor circuit $R_{55}C_{55}$–$R_{61}C_{61}$, respectively, which in turn produces a negative going impulse of 20 milliseconds duration at output pin 1 which in turn is entered in its respective counter/calculator 148–160 through line 21, 24, 27, 30, 33, 36 or 39, respectively. The input lead for the entry of an interger 1 in this fashion is designated as terminal 14 on counter/calculators 148–160.

In the Add mode, switch $S_{14}$ is in the $b$ position which inhibits multivibrators $IC_{35}$–$IC_{41}$ by placing a 9 volt bias on pins 3 thereof. In the Delete mode $S_{14}$ is in the $a$ position which places the 9 volt inhibit voltage on pins 3 of multivibrators $IC_{28}$–$IC_{34}$.

In the Add mode and after the 20 millisecond negative going pulse is entered on lead 14 of counter/calculator 148–160, multivibrators $IC_{15}$–$IC_{20}$ and $IC_{42}$ produce a second 20 millisecond negative going pulse which activates multivibrators $IC_{28}$–$IC_{34}$, respectively, through the appropriate connection 190–198. The triggered multivibrator $IC_{28}$–$IC_{34}$ produces a 20 millisecond negative going impuse which is entered into its respective counter/calculator 148–160 through lines 22, 25, 28, 31, 34, 37, and 40. This causes the counter/calculator to perform an addition operation on the previously entered integer so that the integer 1 is added to the total presently stored therein.

In the Delete mode, switch $S_{14}$ is in the $a$ position thereby placing a 9 volt inhibit bias on multivibrators $IC_{28}$–$IC_{34}$ and removing the bias from multivibrators $IC_{35}$–$IC_{41}$. When one of the multivibrators $IC_{15}$–$IC_{41}$, rather than the adjacent multivibrator $IC_{28}$–$IC_{34}$, will be triggered and will generate an impulse on pin 1 and connecting line 23, 26, 29, 32, 35, 38 and 41, respectively, to enter an instructional command to its respective counter/calculator 148–160 causing an integer 1 to be subtracted from the number previously stored therein. In the Delete mode, the functioning of switches $S_1$–$S_6$ and multivibrators $IC_{15}$-27 and $IC_{42}$ is the same as the Add mode.

As indicated earlier, the timing and spacing of the pulses generated by the various multivibrators is controlled by the resistive-capacitive circuit connected thereto in a manner well known in the art.

Channel 7 counter/calculator 160 is the counter which tabulates the total number of countes entered in individual channels 1–6. When one of switches $S_1$–$S_6$ are closed, the negative impulse on lines 176–178 are also fed into multivibrator $IC_{14}$ by means of lines 200 and 202. The output from multivibrator $IC_{14}$ triggers multivibrator $IC_{42}$ which in turn triggers $IC_{27}$ to place a negative going pulse to line 39 which enters an integer 1 into total counter/calculator 60 by way of terminal 14. The functioning of multivibrators $IC_{34}$ and $IC_{41}$ for the Add and Delete modes is identical to the general operation of the circuitry in FIG. 3B described above.

To prevent a simultaneous entry in two or more of the channels with only a single entry into the channel 7 counter/calculator 160 thereby rendering an inaccurract divisor, means are provided for inhibiting entry into more than one of channels 1–6 when one of the switches $S_1$–$S_6$ is closed. This is accomplished by means of multivibrator $IC_{14}$ which produces a 50 millisecond positive going pulse on pin 6, lines 204, through diodes $D_{21}$–$D_{26}$ and lines 14–19 to multivibrators $IC_{15}$–$IC_{20}$. The presence of this 50 millisecond positive pulse on the input pin to the last mentioned multivibrators has the effect of balancing a negative going pulse from any of switches $S_1S_6$ if same should be actuated during the 50 millisecond folloiwng the triggering of multivibrator $IC_{14}$. After the 50 millisecond inhibit, however, counter/calculator 160 has completed entry of the previous integer and is receptive the entry of another integer. By this time, multivibrators $IC_{15}$–$IC_{20}$ will again be rendered operable by the removal of the positive inhibiting voltage and are capable of being triggered.

As evidenced in the field of hand-held portable calculators, complex counting and operational functions can be achieved by TTL semiconductor chips. These normally employ a multi-digit LED readout which is multiplexed and scanned many times per second to reduce the amount of wiring and to minimize current consumption. Due to the versitility and ease of connection with such calculator chips, it is possible to tailor their operation according to the requirements of the specific application.

Figure 4:
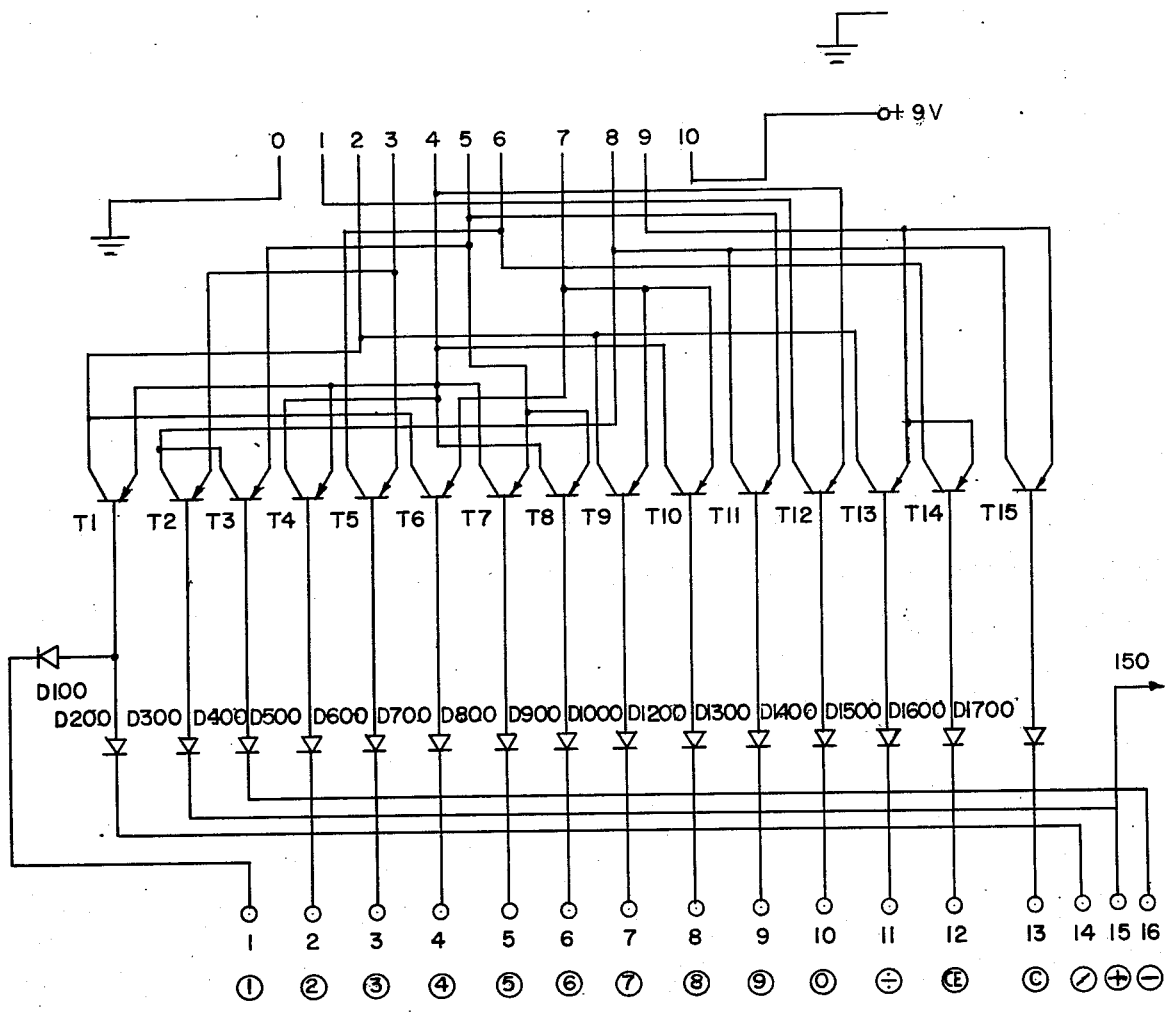
FIG. 4 is an electrical circuit diagram for one of the channels showing the transistor switching network interface between one of the channel inputs and its respective calculator chip.
Figure 5:
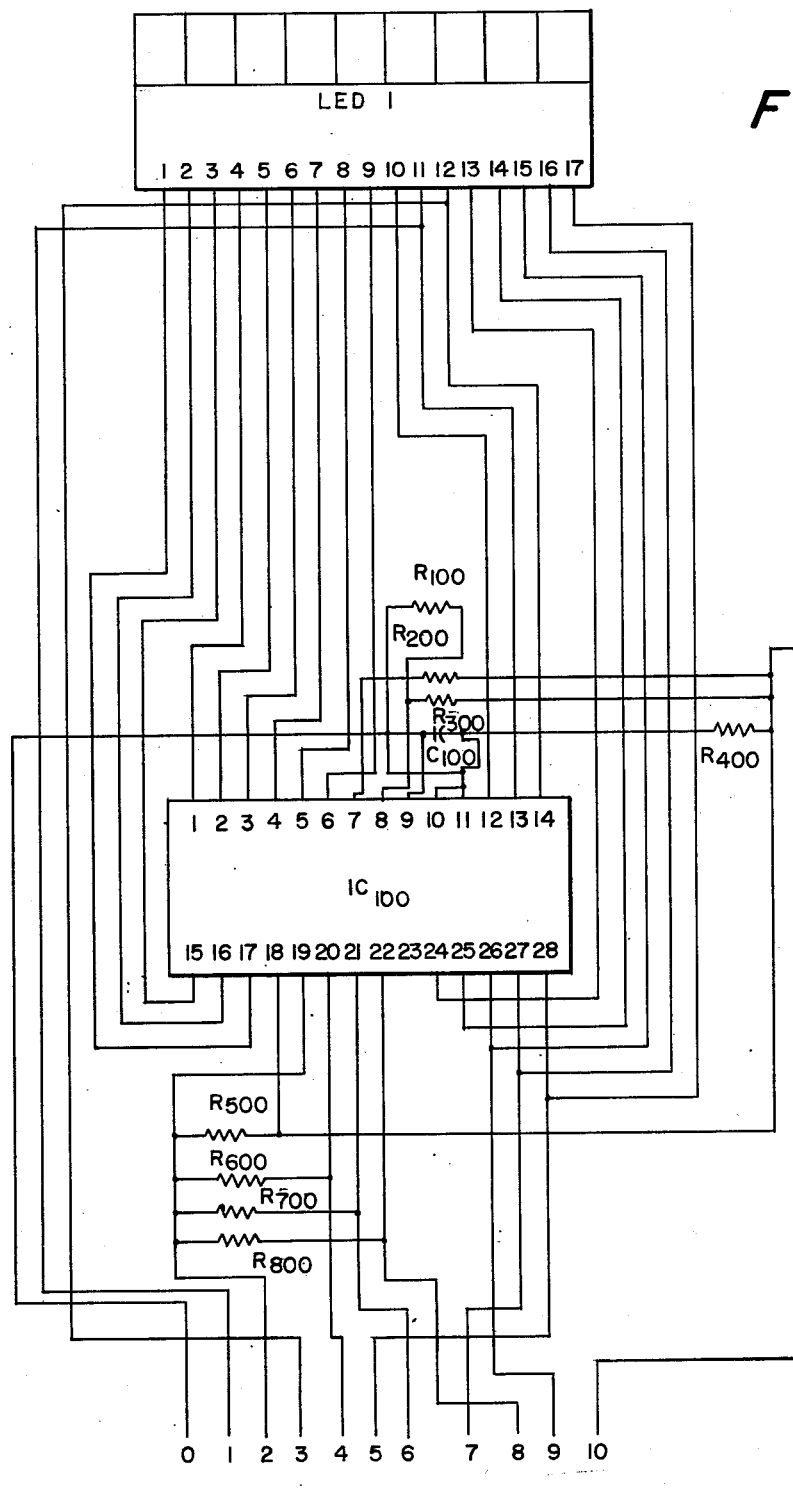
FIG. 5 is an electrical circuit diagram of the calculating chip and LED display and joins with the circuit shown in FIG. 4.

Referring to FIGS. 4 and 5, the counter/calculator chips shown generally in FIG. 3C are illustrated in somewhat greater detail especially with regard to the transistor triggering circuit and its input leads which correspond to the terminals shown on counter/calculator chips 148–160. At the heart of the counter/calculator, is a Texas Instruments calculator chip CP 7541 identified as $IC_{100}$, having terminals numbered consecutively 1 through 28. Due to the complexity of such a calculator chip and the fact that it is commerically available, no details of its construction are included herein. The chip is capable, however, of entering numbers, storing the numbers, performing the mathematical operations of addition, subtraction and division and providing output signals to DED display LED 1 in a manner well known in the art. LED 1 is a universal 9 digit LED display having input pins numbered sequentially from 1 to 17 as illustrated.

In FIG. 4 is illustrated the transistor switching network interface between the pulse generating circuit of FIGS. 3A, 3B and 3C and $IC_{100}$ shown in FIG. 5. The 11 input lines to the calculator chip-LED circuit of FIG. 5 and numbered 0 through 10 correspond to the outputs of the transistor triggered circuit of FIG. 4. Since negative going pulses are utilized to enter data and instructional commands in the counter/calculator, diodes $D_{100}$ through $D_{1700}$ are employed to provide isolation from positive pulses and voltages. Transistors $T_1$–$T_{15}$ are commercially available 2N4917 transistors and connected in such a manner that negative going pulses on individual ones of input terminals 1 through 16 cause triggering of different combinations of output terminals 1 through 9.

The interface circuit, calculator chip and LED display shown in FIGS. 4 and 5 operates generally in the following manner. When a negative going pulse is placed on input terminal 1 in FIG. 4, transistor $T_1$ turns on causing calculator chip $IC_{100}$ to enter the integer 1 therein. If a negative going pulse is then placed on lead 15, the previously entered integer 1 is added to the number previously stored therein and the resultant sum is retained in the memory. A negative pulse on terminal 2 in FIG. 4 turns on transistor $T_4$ Causing the entry an integer 2 in calculator chip $IC_{100}$. A negative pulse on terminal 15 causes the entered integer to be added whereas a negative pulse on terminal 16 following the entry of integer 2 will cause it to be subtracted from the sum previously stored therein and the resultant difference retained in the memory. In like fashion, negative pulses on terminals 3, 4, 5, 6, 7, 8, 9 and 10 causes transistors $T_5$–$T_{12}$, respectively, to be turned on thereby entering the integers 3, 4, 5, 6, 7, 8, 9 and 0, respectively, in calculator chip $IC_{100}$. If negative pulses are sequentially placed on a number of terminals 1 through 10, a multiple digit number will be entered. For example, negative pulses on terminals 3, 8 and 1 in succession will cause the number 381 to be entered. Subsequent negative pulsing of terminal 15 or 16 will cause the entered number to be added or subtracted from the number previously stored therein.

As to the other operational terminals, a negative pulse on terminal 11 sets chip $IC_{100}$ in a state whereby it is receptive for the entry of a divisor. By entering a number and then again pulsing terminal 11, this causes the first number stored in the chip $IC_{100}$ to be divided by the number entered after the first pulsing of terminal 11 to produce a quotient which is the first number divided by the second. A negative pulse on terminal 12 causes the count total to be cleared and pulsing terminal 13 causes the divisor to be cleared. A negative pulse on terminal 14, which comes into play during the Count mode, agan turns on transistor key 1 thereby causing the entry of an integer 1.

Figure 6:
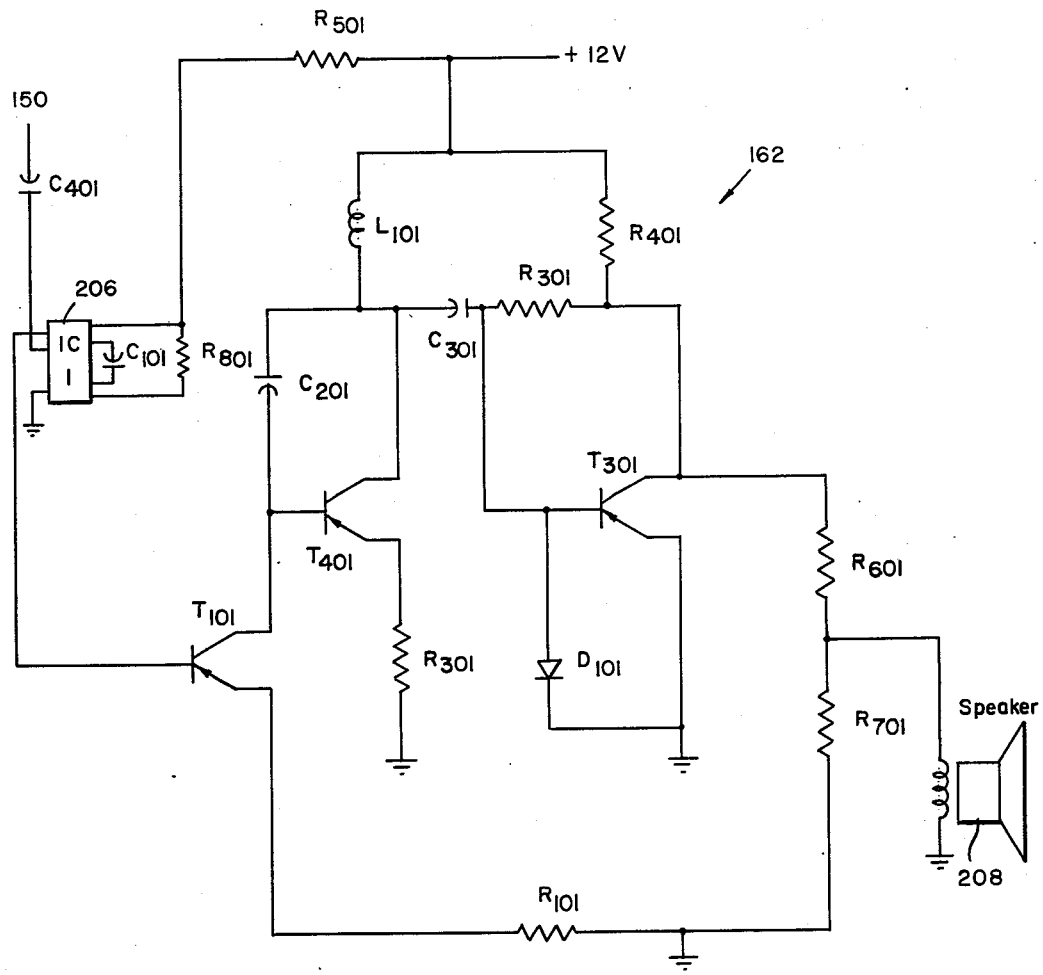
FIG. 6 is an electrical circuit diagram of an oscillator forming a part of the present invention.

Each time terminal 15 is pulsed, thereby signifying the addition of an integer, monostable multivibrator 206 in FIG. 6 is triggered which in turn provides an output pulse to transistor $T_{101}$ thereby causing the oscilallator circuit to produce a short duration tone burst of audio frequency which is emitted by speaker 208. This audio signal indicates to the technician, who is normally observing this sample under the microscope without looking at the tabulator display, that the entry has been registered by the counter/calculator.

It should be noted that the interface circuit illustrated in FIG. 4 and the calculating chip-LED display of FIG. 5 are associated with only a single channel, for example channel 7, which is the total cell count channel. Identical circuits are provided for each of counter/calculators 148–158 and have input terminals 1 through 16 which correspond to those shown in FIG. 3C. With reference to FIG. 3C, all entries into the counter/calculators 148–160 on terminals 1 through 13 inclusive are common to each of them. The lines connecting to terminals 14, 15, and 16, however, which serve to enter individual counts of one in addition to the add or subtract operational commands, are unique to each of the counter/calculator channels. By virtue of monostable multivibrator $IC_{14}$ having an input which is common to switches $S_1$ through $S_6$, however, the entry of an integer 1 into any of counter/calculators 148–158 results in the entry of an integer 1 into the total channel counter/calculator 160 so that a total cell count may be provided.

OPERATION

With the counter/calculators cleared, the technician moves switch 116 to the Count position and switch 118 to the Add position which places switch $S_{13}$ in the *a* position and switch $S_{14}$ in the *b* position. This results in a 9 volt inhibit voltage being placed on Calculate mode multivibrators $IC_1$–$IC_{12}$ and delete function multivibrators $IC_{35}$–$IC_{41}$.

While observing the blood sample under the microscope, the technician depresses one of switches 124, 126, 128, 130, 132 and 134 each time a particular cell corresponding to that channel is observed. For example, assume that a lymphocyte is observed. The technician depresses key 126 which causes switch $S_2$ to be closed thereby placing a negative impulse on line 178 which triggers multivibrator $IC_{16}$. The negative impulse on line 178 is fed to the input of multivibrator $IC_{42}$ through line 200 and connection 20. Multivibrator $IC_2$ will not be triggered due to the positive 9 volt vias on its input through diode $D_2$.

When multivibrator $IC_{16}$ is triggered, it produces a negative going impulse of 25 milliseconds duration which is fed to the input of $IC_{22}$ through RC circuit $R_{56}C_{56}$. Multivibrator $IC_{22}$ in turn produces a negative going impulse of 20 milliseconds duration which is fed to terminal 14 of channel 2 counter/calculator 150 along line 24. Assuming for the moment that the interface circuit and calculating chip illustrated in FIGS. 4 and 5 corresponds to channel 2 counter/calculator 150, the negative going 20 millisecond pulse on terminal 14 will turn on transistor $T_1$ through diode $D_{200}$ thereby triggering the appropriate inputs of calculator chip $IC_{100}$ to enter an integer 1. LED 1 will display this entry. Multivibrator $IC_{16}$ then produces a second negative going pulse from pin 6 which triggers multivibrator $IC_{29}$ at pin 3 through line 192. Although multivibrator $IC_{36}$ is also connected to the output of $IC_{16}$ along line 192, it will not be triggered due to the positive 9 volt inhibit voltage at its input. Multivibrator $IC_{29}$ produces a 20 millisecond negative going pulse which is fed to terminal 15 of counter/calculator 50 along line 25. This causes transistor $T_2$ to turn on which causes chip $IC_{100}$ to perform an addition operation on the previously one thereby yielding a resultant sum of 1 and providing for this display on LED 1.

Since a negative impulse is also present on line 20 of FIGS. 3A and 3B due to the closure of switch $S_2$, multivibrator $IC_{42}$ will be triggered to produce a 25 millisecond negative pulse which triggers multivibrator $IC_{21}$ to produce a 20 millisecond negative going impulse on line 39 and terminal 14 of the Total counter/calculator 60. Assuming for the moment that the interface circuit and calculating chip shown in FIGS. 4 and 5 corresponds to channel 7 counter/calculator 60 rather than counter/calculator 50, the negative impulse on terminal 14 causes transistor $T_1$ to turn on thereby entering an integer 1 in chip $IC_{100}$ which causes display of this number on LED 1.

Multivibrator $IC_{42}$ will then produce a second negative going pulse which triggers multivibrator $IC_{34}$ to produce a 20 millisecond negative going pulse on line 40 and lead 15 of counter/calculator 160. The pulse on terminal 15 turns on transistor $T_2$ thereby causing chip $IC_{100}$ to perform an addition function on the previously entered integer 1. As will be recalled, $IC_{41}$, although connected to multivibrator $IC_{42}$ by line 198, will not be activated due to the 9 volt inhibit voltage present at its input to diode $D_{27}$. When the addition function pulse is fed to terminal 15 of the interface circuit in FIG. 4, line 150 will feed a negative pulse to multivibrator 206 in FIG. 6 thereby causing the oscillator to generate a short duration tone which is acoustically reproduced by speaker 208. The technician will therefore be aware that the entry has been made without the necessity for looking up from the slide which he is observing in the microscope. At this point in time, an integer 1 is stored in counter/calculator 150 and counter/calculator 160 and is displayed on their corresponding LED 1 displays.

Assume now that the technician observes a basophil. He will depress key 132 thereby closing switch $S_5$ and placing a negative impulse on line 184 which in turn triggers multivibrator $IC_{19}$ through line 18. A negative going pulse will also be transmitted to multivibrator $IC_{42}$ through lines 220. Multivibrator $IC_{19}$ will produce a 25 millisecond negative going impulse which triggers adjacent multivibrator $IC_{25}$ thereby placing a 20 millisecond negative going impulse on line 33 and terminal 14 of counter/calculator 156. Again assuming for the moment that the circuitry in FIGS. 4 and 5 represents counter/calculator 156, the negative impulse on terminal 14 turns on transistor $T_1$ and enters an integer 1 into chip $IC_{100}$. Multivibrator $IC_{19}$ will then produce a second negative going impulse of 20 milliseconds duration which triggers multivibrator $IC_{32}$ through line 195. Multivibrator $IC_{32}$ produces a 20 millisecond negative going impulse and feeds this to terminal 15 of counter/calculator 156 along line 34. This turns on transistor $T_2$ and causes chip $IC_{100}$ to perform an addition operation on the previously entered integer 1 thereby producing a resultant sum of 1 in the memory and displaying this on LED 1.

Since $IC_{42}$ has also been triggered simultaneously with $IC_{19}$, it will emit a negative going pulse to trigger multivibrator $IC_{27}$ which feeds a negative pulse to terminal 14 and counter/calculator 160 along line 39. Assuming for the moment that the circuitry of FIGS. 4 and 5 represents counter/calculator 160, this will turn on transistor $T_1$ and enter an integer 1 in chip $IC_{100}$ which in turn displays this integer 1 on LED 1. Multivibrator $IC_{42}$ then produces a second negative going pulse on line 198 which triggers multivibrator $IC_{34}$ to produce a 20 millisecond negative going impulse on line 40 and terminal 15 of counter/calculator 160. This turns on transistor $T_2$ to add the previously entered integer 1 to the integer 1 which is already stored therein by virtue of the entry of the lymphocyte observation to produce a resultant sum of 2 which is then displayed on LED 1. The negative pulse on line 150 causes the oscillator of FIG. 6 to emit a short tone through speaker 208. At this point in time, counter/calculator 150 is storing and displaying an integer 1, counter/calculator 156 an integer 1 and counter/calculator 160 is storing an integer 2.

In the two operations described above, multivibrator $IC_{14}$ is triggered by virtue of the negative pulse on lines 200 and 202 and produces a 50 millisecond positive going impulse on pin 6 which is transmitted to the inputs of multivibrators $IC_{15}$–$IC_{20}$ and $IC_{42}$ through diodes $D_{21}$–$D_{26}$ and $D_{14}$, and lines 14–20, respectively. This inhibits the triggering of multivibrators $IC_{15}$–$IC_{20}$ and $IC_{42}$ for a period of approximately 50 milliseconds. Although the multivibrator $IC_{15}$–$IC_{20}$ and $IC_{42}$ which is connected directly to switches $S_1$–$S_6$ has already been triggered by the time the 50 millisecond pulse reaches its input, rapid closure of another switches $S_1$–$S_6$ will be unable to cause a subsequent triggering until the positive voltage is removed after the inhibit period. This is necessary to prevent entry into two or more of channels 1 through 6 in rapid succession before channel 7 is able to respond to the second entry. If this were to occur, the count stored in the channel 7 counter/calculator 160 would be lower than the total of all counts stored in channels 1 through 6. Since the 50 millisecond time period is very short in relation to the ability of the technician to rapidly depress two switches in succession under normal counting conditions, it has no appreciable affect on the effeciency of the device.

If the technician observes another lymphocyte, he will depress key 126 thereby triggering multivibrators $IC_{16}$ and $IC_{22}$ to enter an integer 1 in counter/calculator 150, with the second negative pulse from multivibrator $IC_{16}$ triggering multivibrator $IC_{29}$ to add this second entered integer 1 to the integer 1 previously stored therein and causing its associated LED 1 to display an integer 2. Simultaneously, multivibrator $IC_{42}$ will be triggered which in turn triggers multivibrators $IC_{27}$ and $IC_{34}$ to enter an integer 1 into counter/calculator 160 which is added to the integer to previously stored therein thereby displaying an integer 3 as the resultant sum. Since multivibrator $IC_{14}$ will also be triggered, a 50 millisecond positive going inhibit pulse will be placed on the inputs to multivibrators $IC_{15}$-$IC_{20}$ and $IC_{42}$ shortly after multivibrators $IC_{16}$ and $IC_{42}$ are triggered.

Should the technician make a mistake and press key 130 when he intended to depress key 128, multivibrator $IC_{18}$ will be triggered causing multivibrators $IC_{24}$ to pulse terminal 14 of counter/calculator 154 thereby entering an integer 1 into its calculating chip $IC_{100}$. The second negative pulse from multivibrator $IC_{18}$ will trigger $IC_{31}$ to enter an Add pulse on terminal 15 of counter/calculator 154. Simultaneously, multivibrator $IC_{42}$ will be triggered to enter and add an integer 1 to counter/calculator 160. At this point, counter/calculator 150 will display a 2, counter/calculator 156 a 1, counter/calculator 154 a 1 and counter/calculator 160 a 4. To correct the improper entry, the technician moves switch 118 to the Delete position which places a 9 volt inhibit voltage on terminal $a$ of switch 14 thereby inhibiting multivibrators $IC_{28}$-$IC_{34}$ and removing the inhibit voltage from multivibrators $IC_{35}$-$IC_{41}$. The technician will then again depress key 130 which closes switch $S_4$ and triggers multivibrator $IC_{18}$. $IC_{18}$ produces a first negative going pulse of 25 millisecond duration which triggers adjacent multivibrator $IC_{24}$ to enter an integer 1 into counter/calculator 154. The second negative pulse from multivibrator $IC_{18}$ will be fed to the input of multivibrator $IC_{38}$ along line 194 which in turn produces a negative pulse at terminal 16 of counter/calculator 154 along lines 32. Again assuming the circuitry in FIGS. 4 and 5 represents counter/calculator 154, the negative pulse on terminal 16 will cause transistor $T_3$ to turn on thereby entering a delete function pulse to chip $IC_{100}$ which has the effect of subtracting an integer 1 to the integer 1 previously stored therein. When this is done, LED 1 will display a zero.

Simultaneously, multivibrator $IC_{42}$ will initiate a sequence of events to enter an integer 1 into counter/calculator 160 and the second pulse along line 198 will not activate multivibrator $IC_{34}$ due to the 9 volt inhibit voltage and will trigger multivibrator $IC_{41}$ to produce a negative going pulse on line 41 and a terminal 16 of counter/calculator 160. In a similar fashion to counter/calculator 154, this will cause the previously entered integer 1 to be subtracted from the number 4 previously stored and the resulting integer 3 which is from that point on displayed on LED 1.

To make the correct entry, switch 118 is again moved to the Add position and the correct key depressed.

Should it be desired to clear all of channels 1-7, switch 116 is moved to the Count position and key 138 depressed. This closes switch $S_{12}$ which triggers multivibrator $IC_{13}$ to produce a negative going pulse on line 13 thereby turning on transistor $T_{15}$ in all of counter/calculators 148-160. This causes the totals stored therein to be cleared and a zero to be displayed by their respective displays LED 1.

Assuming the technician has counted and entered 140 cells and that the stored and displayed numbers for each of the channels is as follows:

Counter/Calculator 49 (monocytes). 3
Counter/Calculator 50 (lymphocytes): 67
Counter/Calculator 52 (neutrophils): 60
Counter/Calculator 54 (eosenophils): 4
Counter/Calculator 56 (basophils): 1
Counter/Calculator 58 (stabs): 5
Counter/Calculator 60 (total): 140

The technician then moves switch 116 to the Calculate position which causes switch $S_{13}$ to place a 9 volt inhibit voltage on terminal $b$ and at the inputs to multivibrators $IC_{15}$-$IC_{20}$ and $IC_{42}$ through lines 14-20, respectively. At the same time, the inhibit voltage is removed from the inputs to multivibrators $IC_1$-$IC_{12}$. Since the total number of cells counted is 140, the technician enters this number into each of the counter/calculators 148-160. This is done by first depressing key 138 which closes switch $S_{11}$ thereby triggering multivibrator $IC_{11}$ to transmit a negative pulse over line 11 to input terminal 11 of each counter-calculator 148-150. In each channel, this turns on transistor $T_{13}$ which sets the respective chips $IC_{100}$ ready for the entry of a common divisor. The total number appearing in window 122, which in this case is 140 is then entered by sequentially depressing keys 124, 130 and 210. This triggers multivibrators $IC_1$, $IC_4$, $IC_{10}$ to transmit negative pulses to the input terminals 1, 4 and 10 of each of the counter/calculators 148-160 thereby turning on transistors $T_1$, $T_6$ and $T_{12}$. This causes each $IC_{100}$ to enter the number 140 and this number will be displayed in each of the channel displays LED 1. After the numerical value has been entered, key 38 is again depressed which triggers $IC_{11}$ to enter the divide-by function on terminal 11 which in turn turns on transistor $T_{13}$ to cause each calculating chip $IC_{100}$ to divide the individual counts stored therein by the common division which has just been entered.

The numbers then displayed by the appropriate channel LED's and visible through windows 20 and 22 are the following:

Counter/Calculator 48 (monocytes): .02
Counter/Calculator 50 (lymphocytes): .48
Counter/Calculator 52 (neutorphils): .43
Counter/Calculator 54 (eosenophils): .03
Counter/Calculator 56 (basophils): .01
Counter/Calculator 58 (stabs): .03
Counter/Calculator 60 (total): 1.00

Since the numbers which are then stored and displayed are equal to the individual counts divided by the total cell count, the represent the decimal fraction of each cell to the total cells. By disregarding the decimal point, the numbers so displayed are the percentages of each cell observed by the technician. Since the device includes means for dividng the individual cell counts by the total, it is not necessary for the technician to stop the count at 100 but can continue as long as he wishes without the need for performing manual computations.

If a mistake is made in the entry of the divisor, depression of key 136 in the Calculate mode will close switch $S_{12}$ thereby triggering multivibrator $IC_{13}$ to enter a negative pulse on terminal 13 of each channel counter/calculator 148-160 which turns on the respective transistors $T_{15}$ to clear the divisor therefrom. The total accumulated counts stored in each channel remain, however.

If desired, a second oscillator 212 may be connected to terminals 14 and 16 of counter/calculator 60 through an electronic counter 214. The purpose of this is to emit an audible signal whenever 100 counts are entered in counter/calculator 160. Each time a negative pulse is sensed on terminal 15, the counter with the advanced by an increment of 1 and each time a pulse is present on terminal 16, which occurs when an interger 1 is being deleted from the counter/calculator 160, counter 214 would be backed up by one. Oscillator 212 will sound when a total count of 100 is registered by counter 214.

The following components may be employed in construction of the tabulating device described herein:

| | |
|---|---|
| $S_1$-$S_{12}$ Switching Panel | $R_{33}$-$R_{43}$ 100k ohm |
| $S_{13}$ SPST | $R_{44}$ 33 ohm |
| $S_{14}$ SPST | $R_{45}$ 100k ohm |
| $D_1$-$D_{40}$ 1N914 | $R_{46}$ 100 k ohm |
| Multivibrators $IC_1$-42 SN 74121 | $R_{47}$-54 2200 ohm |
| $R_1$-$R_{14}$ 100k ohms | $R_{55}$-$R_{61}$ 100 k ohm |
| $R_{15}$-$R_{32}$ 33 ohms | $R_{62}$-75 33 ohm |
| $R_{76}$-82 100 k ohm | $R_{300}$ 100 k ohm |
| $R_{83}$-89 33 ohm | $R_{500}$-$R_{800}$ 330 ohm |
| $R_{90}$-96 100 k ohm | $C_{100}$ 25 pf |
| $C_1$-14 .001 mf | $C_{101}$ 20 mf |
| $C_{15}$-32 20 mf | $C_{201}$ .1 mf |
| $C_{33}$-43 .001 mf | $C_{301}$ 1 mf |
| $C_{44}$ 20 mf | $C_{401}$ .001 mf |
| $C_{45}$, $C_{46}$ 1001 mf | $R_{101}$ 4.4 k ohm |
| $C_{47}$-54 20 mf | $R_{201}$ 2.2 k ohm |
| $C_{55}$-61 .001 mf | $R_{301}$ 68 k ohm |
| $C_{62}$-75 20 mf | $R_{401}$ 1.5 kohm |
| $C_{76}$-82 .001 mf | $R_{601}$ 2.2 k ohm |
| $C_{83}$-89 20 mf | $R_{701}$ 2.2 k ohm |
| $C_{90}$-96 .001 mf | $D_{101}$ 1N914 |
| $D_{100}$-$D_{1700}$ 1N914 | $T_{101}$ 2N4917 |
| $T_1$-$T_{15}$ 2N917 | $T_{201}$ 2N414 |
| LED 1 Universal 9 Digit | Multivibrator $IC_{206}$ SN 74121N |
| $IC_{100}$ TMC 0952 $N_1$ 7528 | $R_{801}$ 1 k ohm |
| $R_{100}$ 56 k ohm | $L_{101}$ 4 Hy |
| $R_{200}$, $R_{400}$ 58 k ohm | Spkr. 208 3.2 ohm speaker |

Although the preferred embodiment has been described as comprising a large number of independently wired electronic elements, it is possible to incorporate the entire circuit into a single chip using present technology. Alternate circuits using parallel counting and dividing register can also be complexed in a single chip. Displays such as liquid crystal displays, nixie tubes, etc. are also feasible in lieu of the LED displays. Furthermore, any number of Count channels could be provided and is not limited to six.

While this invention has been described as having a preferred design, it will be understood that it is capable of further modification. This application is, therefore, intended to cover any variations, uses, or adaptations of the invention following the general principles thereof and including such departures from the present disclosure as come within known or customary practice in the art to which this invention pertains, and as may be applied to the essential features hereinfore set forth and fall within the scope of this invention or the limits of the appended claims.

What is claimed is:

1. An electronic calculator-register for hematology differentials comprising:
   A. a plurality of counter-calculator means for storing numbers entered therein and performing mathematical computations on said entered numbers in response to instructional commands entered therein,
   B. dual purpose keyboard means coded for the first purpose of visibly detecting specific types of blood cells and manually entering said cells in a one-by-one fashion and including a plurality of input elements coded for the second purpose of introducing numerical data and instructional commands in response to the operation of said input elements,
   C. switching network means operatively connected said keyboard entry means and said plurality of counter-calculator means for entering into said counter-calculator means said data and instructional commands introduced by said keyboard means,
   D. said switching network means including first means for operatively connecting each of a first selected plurality of said input elements to different ones of a selected plurality of said counter-calculator means, and for entering an interger 1 corresponding to the specific blood cell type visibly detected in one of said counter-calculator means and instructing one of said counter-calculator means to add the entered integer 1 to the numbers stored therein and to store the resultant sum of detected blood cells when the respective said input element is operated,
   E. said switching network means including second means for operatively connecting said first selected plurality of input elements to another of said counter-calculator means and for entering an interger 1 in said counter-calculator means and instructing said last mentioned counter-calculator to add the entered integer 1 to the number stored therein and to store the resultant sum when any of said first selected plurality of input elements is operated,
   F. said switching network means including third means for operatively connecting each of a second plurality of input elements to each of said first selected plurality of counter-calculator means and for entering a number and instructional commands therein causing each of said counter-calculator means to effectively divide the resultant sum previously stored therein by the second number and store resultant quotient, and
   G. display means associated with each of said counter-calculator means for displaying numbers currently stored therein.

2. The apparatus of claim 1 wherein:
said switching network means has a count mode and a calculate mode and manually operable means for switching said switching network between said count and calculate modes,
said keyboard means comprises a plurality of manually operable switches, a first part of said switches being operatively connected to said first plurality of input elements when said switching network means is in said count mode and said first part of said switches being operatively connected to some of said second plurality of input elements when said switching network means is in said calculate mode.

3. The apparatus of claim 1 wherein:
said keyboard means comprises a plurality of manually operable switches,
said counter-calculator means includes a plurality of input leads and means associated with said leads for entering and storing numbers and performing operations in response to input pulses received on selected ones of said leads,
said switching network means including a plurality of monostable multivibrator means for generating command and data pulses and feeding said pulses to selected ones of said leads in response to the closing of selected said switches.

4. The apparatus of claim 1 and including means operatively connected to said another of said counter-calculator means for generating a first audible signal when an interger is entered therein.

5. The apparatus of claim 4 and including means for generating a second audible signal when a total of one hundred intergers has been entered in said anotherof said counter-calculator means.

6. The apparatus of claim 1 and including means for inhibiting the entry of a subsequent interger in said another of said counter-calculator means during a given period of time subsequent to the entry of the preceeding integer.

7. The apparatus of claim 1 wherein said display means comprises an individual LED display for each of said counter-calculator means.

8. The apparatus of claim 1 wherein said switching network means includes:

Selectively operable means for deleting an integer 1 from one of said selected plurality of said counter-calculator means when its respective said input element is operated and for deleting an interger 1 from said another of said counter-calculator means when said respective input element is operated.

* * * * *